US012711681B2

(12) United States Patent
Nishioka

(10) Patent No.: US 12,711,681 B2
(45) Date of Patent: Aug. 18, 2026

(54) RECONSTRUCTION DEVICE, X-RAY CT APPARATUS, AND IMAGE PROCESSING DEVICE

(71) Applicant: Canon Kabushiki Kaisha, Tokyo (JP)

(72) Inventor: Takahiko Nishioka, Otawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 168 days.

(21) Appl. No.: 18/467,855

(22) Filed: Sep. 15, 2023

(65) Prior Publication Data

US 2024/0095977 A1 Mar. 21, 2024

(30) Foreign Application Priority Data

Sep. 16, 2022 (JP) ................................ 2022-148343
Sep. 14, 2023 (JP) ................................ 2023-149063

(51) Int. Cl.
*G06T 12/20* (2026.01)
*A61B 6/03* (2006.01)
*G06T 12/10* (2026.01)

(52) U.S. Cl.
CPC .............. *G06T 12/10* (2026.01); *G06T 12/20* (2026.01); *A61B 6/032* (2013.01); *G06T 2210/41* (2013.01)

(58) Field of Classification Search
CPC ....... G06T 11/006; A61B 6/032; A61B 6/486; A61B 6/503; A61B 6/5264
See application file for complete search history.

(56) References Cited

U.S. PATENT DOCUMENTS 6,915,005 B1 * 7/2005 Ruchala .................. G06T 12/10 382/284
7,426,256 B2 9/2008 Rasche et al.
11,138,768 B2 10/2021 Helm et al.
2006/0210019 A1 * 9/2006 Rasche ................ A61B 6/5264 378/62
2016/0335785 A1 * 11/2016 Joskowicz .............. G06T 12/10
2017/0042494 A1 * 2/2017 Kim ..................... A61B 6/5205
2017/0249740 A1 * 8/2017 Brehm ................ A61B 6/5235
2019/0311505 A1 * 10/2019 Helm ...................... G06T 12/10
2022/0028131 A1 1/2022 Helm et al.
2023/0079025 A1 * 3/2023 Tanaka .................. A61B 5/113 600/534

FOREIGN PATENT DOCUMENTS

JP 4714677 B2 6/2011
JP 2017-15655 A 1/2017
JP 2017015655 A * 1/2017
JP 2021-519646 A 8/2021

* cited by examiner

*Primary Examiner* — Bobbak Safaipour
*Assistant Examiner* — Ashley Hytrek
(74) *Attorney, Agent, or Firm* — Oblon, McClelland, Maier & Neustadt, L.L.P.

(57) ABSTRACT

A reconstruction device according to an embodiment includes a processing circuit. The processing circuit acquires a plurality of pieces of second sinogram data based on a plurality of pieces of first sinogram data, acquires third sinogram data by comparing the pieces of first sinogram data with the pieces of second sinogram data and by selecting pieces of first sinogram data having close similarity, and reconstructs an image on the basis of the third sinogram data.

9 Claims, 5 Drawing Sheets

X-RAY CT APPARATUS
1
GANTRY DEVICE
10
IMAGE PROCESSING DEVICE
40
11
13
16
17
14
P
33
12
DAS
18
CONTROL DEVICE
15
Y
Z
X
MEMORY
41
DISPLAY
42
INPUT INTERFACE
43
PROCESSING CIRCUIT
44
CONTROL FUNCTION
44a
THIRD GENERATION FUNCTION
44e
PRE-PROCESSING FUNCTION
44b
FOURTH GENERATION FUNCTION
44f
FIRST GENERATION FUNCTION
44c
ACQUISITION FUNCTION
44g
SECOND GENERATION FUNCTION
44d
10
BED APPARATUS
30
P
33
34
32
31

FIG.2

RECONSTRUCTION DEVICE, X-RAY CT APPARATUS, AND IMAGE PROCESSING DEVICE

CROSS-REFERENCE TO RELATED APPLICATIONS

This application is based upon and claims the benefit of priority from Japanese Patent Application No. 2022-148343, filed on Sep. 16, 2022; and Japanese Patent Application No. 2023-149063, filed on Sep. 14, 2023; the entire contents of which are incorporated herein by reference.

FIELD

Embodiments described herein relate generally to reconstruction devices, X-ray CT apparatuses, and image processing devices.

BACKGROUND

In cardiac computed tomography angiography (CTA), for example, an artifact, such as a motion artifact, may appear in some cases. A possible method for removing such an artifact is to change the values of pixels in an image where it is considered that an artifact exists, using a deep learning or numerical analysis method or the like.

Unfortunately, with this method, image data itself is changed, so that anatomical information, such as a stricture, may be changed by artifact correction. Thus, it is desirable to correct an artifact without changing a value of image data.

BRIEF DESCRIPTION OF THE DRAWINGS

FIG. 2 is a flowchart illustrating a flow of processing performed by the X-ray CT apparatus according to the embodiment;

DETAILED DESCRIPTION

A reconstruction device provided in one aspect of the present invention includes a processing circuit. The processing circuit acquires a plurality of pieces of second sinogram data from a plurality of pieces of first sinogram data by removing an artifact or noise, acquires third sinogram data by comparing the pieces of first sinogram data with the pieces of second sinogram data and by selecting pieces of first sinogram data having close similarity, and reconstructs an image on the basis of the third sinogram data.

Figure 1:
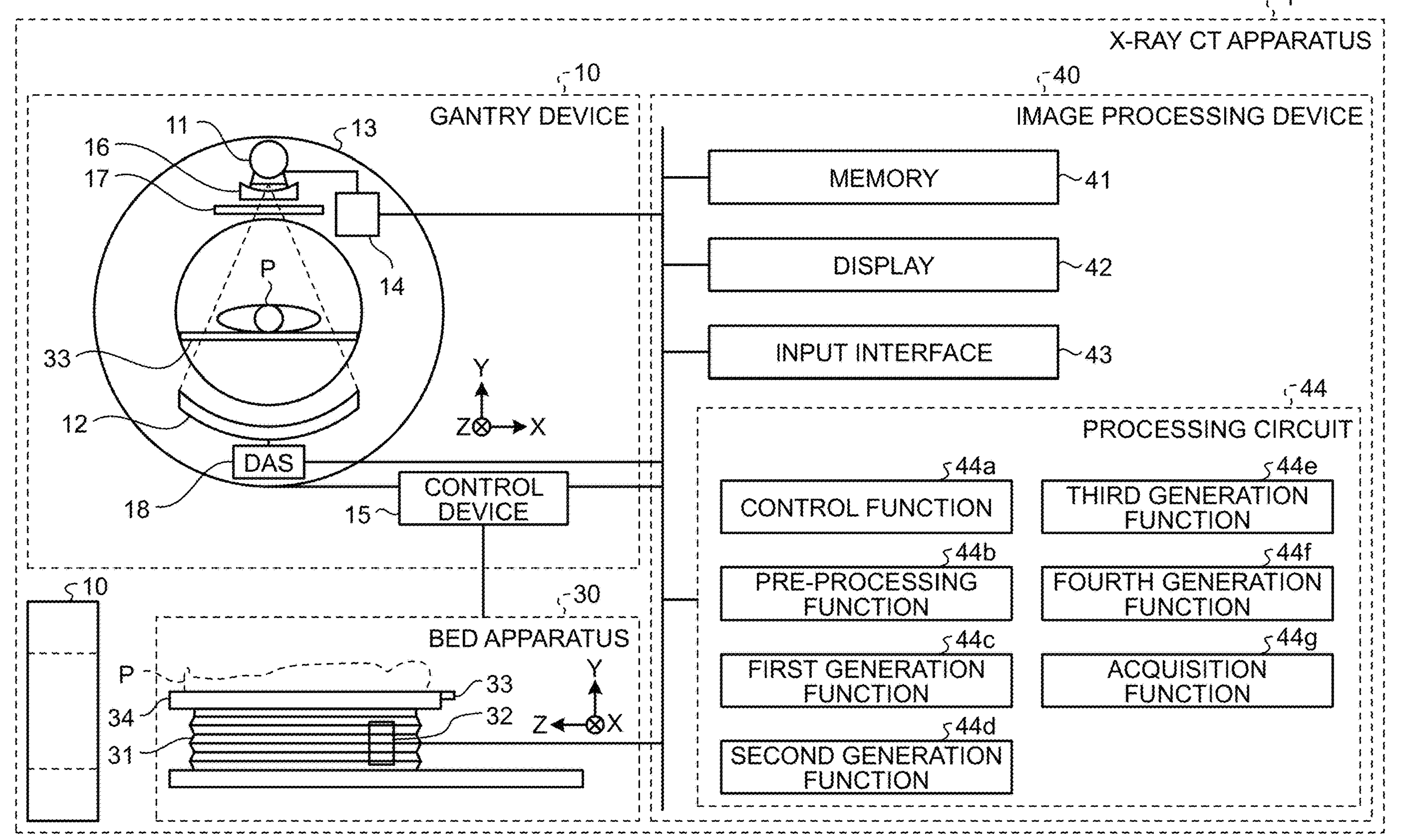
FIG. 1 is a diagram illustrating an example configuration of an X-ray CT apparatus according to an embodiment.

As illustrated in FIG. 1, an X-ray CT apparatus 1 according to an embodiment includes a gantry device 10, bed apparatus 30, and an image processing device 40. Note that FIG. 1 illustrates the gantry device 10 from a plurality of directions for the purpose of explanation and illustrates a case where the X-ray CT apparatus 1 includes a single gantry device 10.

The gantry device 10 includes an X-ray tube 11, an X-ray detector 12, a rotary frame 13, an X-ray high-voltage device 14, a control device 15, a wedge 16, a collimator 17, and a data acquisition system (DAS) 18.

The X-ray tube 11 is a vacuum tube including a cathode (filament) generating thermoelectrons and an anode (target) generating X-rays in response to collision of the thermoelectrons. Application of high voltage from the X-ray high-voltage device 14 causes the X-ray tube 11 to emit thermoelectrons from the cathode toward the anode to generate X-rays to be radiated to a subject P. An example of the X-ray tube 11 is a rotating anode X-ray tube that generates X-rays by emitting thermoelectrons to a rotating anode.

Note that the X-ray tube 11 and the control device 15 are an example X-ray radiation section. The X-ray radiation section executes a low-flux scan of a phantom composed of a known substance and having a known transmission length. Specifically, the X-ray radiation section executes a low-flux scan by executing an air scan and a scan of a phantom composed of a plurality of different substances at settings of an initial current strength and each tube voltage of the X-ray tube.

The rotary frame 13 is an annular frame supporting the X-ray tube 11 and the X-ray detector 12 in opposite positions and rotating the X-ray tube 11 and the X-ray detector 12 using the control device 15. For example, the rotary frame 13 is a casting made from aluminum. Note that the rotary frame 13 can further support the X-ray high-voltage device 14, the wedge 16, the collimator 17, the DAS 18, and the like, in addition to the X-ray tube 11 and the X-ray detector 12. Furthermore, the rotary frame 13 can further support various constituents not illustrated in FIG. 1.

The wedge 16 is a filter for adjusting the dose of X-rays radiated from the X-ray tube 11. Specifically, the wedge 16 is a filter transmitting and attenuating X-rays radiated from the X-ray tube 11 so that the X-rays radiated from the X-ray tube 11 to the subject P have predetermined distribution. For example, the wedge 16 is a wedge filter or a bow-tie filter, and is a filter made from aluminum or the like processed so as to have a predetermined target angle and a predetermined thickness.

The collimator 17 is a lead plate or the like for narrowing the radiation range of X-rays having passed through the wedge 16, and a plurality of the lead plates or the like are combined to define a slit. Note that the collimator 17 may also be called an X-ray limiter. FIG. 1 illustrates a case where the wedge 16 is disposed between the X-ray tube 11 and the collimator 17; however, the collimator 17 may be disposed between the X-ray tube 11 and the wedge 16. In this case, the wedge 16 transmits and attenuates X-rays radiated from the X-ray tube 11 and having its radiation range limited by the collimator 17.

The X-ray high-voltage device 14 includes a high-voltage generator including electric circuits, such as a transformer and a rectifier, and generating high voltage applied to the X-ray tube 11 and an X-ray controller controlling output voltage in accordance with X-rays generated by the X-ray tube 11. The high-voltage generator may be of a transformer type or of an inverter type. Note that the X-ray high-voltage device 14 may be disposed in the rotary frame 13 or in a fixed frame, which is not illustrated.

The control device 15 includes a processing circuit including a central processing unit (CPU) and the like and a driving mechanism, such as a motor and an actuator. The control device 15 controls workings of the gantry device 10 and the bed apparatus 30 in response to input signals from an input interface 43. For example, the control device 15 controls rotation of the rotary frame 13, tilting of the gantry device 10, workings of the bed apparatus 30 and a tabletop 33, and the like. Note that the control device 15 may be disposed in the gantry device 10 or in the image processing device 40.

The X-ray detector 12 is, for example, a photon-counting detector or an energy-integrating detector. When the X-ray detector 12 is a photon-counting detector, each time an X-ray photon being a photon originating from an X-ray radiated from the X-ray tube 11 and having passed through the subject P is incident, the X-ray detector 12 outputs a signal with which the energy value of the X-ray photon can be measured. The X-ray detector 12 includes a plurality of X-ray detecting elements that output one pulse of an electric signal (analog signal) each time the X-ray photon is incident.

For example, in the X-ray detecting element, an anode electrode and a cathode electrode are disposed on a semiconductor device (semiconductor detecting device), such as cadmium telluride (CdTe) or cadmium zinc telluride (CdZnTe).

The X-ray detector 12 includes the X-ray detecting elements and a plurality of application specific integrated circuits (ASIC) connected to the X-ray detecting elements and being readout circuits that count the X-ray photons detected by the X-ray detecting elements. The ASICs discriminate individual electric charges output by the X-ray detecting elements to count the number of the X-ray photons incident on the detecting elements. The ASICs also perform computation based on the magnitude of the individual electric charges to measure the energy of the X-ray photons counted. Furthermore, the ASICs output a result of counting the X-ray photons to the DAS 18 as digital data.

The DAS 18 generates detection data on the basis of the result of the counting input from the X-ray detector 12. The detection data is, for example, sinogram. The sinogram is data in which the results of counting the X-ray photons incident on each X-ray detecting element in each position of the X-ray tube 11 are arranged. The sinogram is data in which the results of the counting are arranged in a two-dimensional orthogonal coordinate system with axes in the view direction and the channel direction. The DAS 18 generates sinogram per column in the slice direction in the X-ray detector 12, for example. The DAS 18 transfers the generated detection data to the image processing device 40. The DAS 18 is implemented by, for example, a processor.

The data generated by the DAS 18 is transmitted by optical communications from a transmitter disposed in the rotary frame 13 and including a light emitting diode (LED) to a receiver disposed in a non-rotary part (for example, the fixed frame or the like, which is not illustrated in FIG. 1) of the gantry device 10 and including a photodiode, and is transferred to the image processing device 40. Herein, the non-rotary part is, for example, the fixed frame rotatably supporting the rotary frame 13, or the like. Note that the method of transmitting data from the rotary frame 13 to the non-rotary part of the gantry device 10 is not limited to optical communications, and any non-contact data transmission method or a contact data transmission method may be used.

The bed apparatus 30 is a device for placing and moving the subject P to be imaged and includes a base 31, a table driving device 32, the tabletop 33, and a supporting frame 34. The base 31 is a housing supporting the supporting frame 34 in a vertically movable manner. The table driving device 32 is a driving mechanism moving the tabletop 33 on which the subject P is placed in the long axis direction of the tabletop 33 and includes a motor, an actuator, and the like. The tabletop 33 disposed on a top surface of the supporting frame 34 is a plate on which the subject P is placed. Note that the table driving device 32 may move the supporting frame 34 in the long axis direction of the tabletop 33, in addition to the tabletop 33.

The image processing device 40 includes a memory 41, a display 42, the input interface 43, and a processing circuit 44. Note that the image processing device 40 is described as a constituent separate from the gantry device 10; however, the gantry device 10 may include the image processing device 40 or some constituents of the image processing device 40.

The memory 41 is implemented by, for example, a semiconductor memory device, such as a random access memory (RAM) or a flash memory, a hard disk, an optical disk, or the like. The memory 41 stores therein, for example, projection data and CT image data. For example, the memory 41 stores therein a computer program with which circuits included in the X-ray CT apparatus 1 realize various functions. The memory 41 may be implemented by a group of servers (cloud) connected to the X-ray CT apparatus 1 via a network.

The display 42 displays various pieces of information. For example, the display 42 displays various images generated by the processing circuit 44 and displays a graphical user interface (GUI) for receiving various operations from an operator. For example, the display 42 is a liquid crystal display or a cathode ray tube (CRT) display. The display 42 may be of a desktop type or may be configured by a tablet terminal or the like that can wirelessly communicate with the main body of the image processing device 40. The display 42 is an example display section.

The input interface 43 receives various input operations from the operator, converts the received input operations into electric signals, and output the signals to the processing circuit 44. For example, the input interface 43 receives, from the operator, input operations regarding scan conditions, reconstruction conditions when CT image data is reconstructed, image processing conditions when a post-processed image is generated from CT image data, and the like.

For example, the input interface 43 is implemented by a mouse, a keyboard, a track ball, a switch, a button, a joystick, a touch pad enabling input operations by touch on an operation surface, a touch screen in which a display screen and a touch pad are integrated, a non-contact input circuit using an optical sensor, a voice input circuit, or the like. Note that the input interface 43 may be disposed on the gantry device 10. The input interface 43 may be configured by a tablet terminal or the like that can wirelessly communicate with the main body of the image processing device 40. The input interface 43 is not limited to an object including a physical operation component, such as a mouse or a keyboard. For example, an example of the input interface 43 also includes an electric signal processing circuit that receives an electric signal corresponding to an input operation from an external input device provided separate from the image processing device 40 and outputs the electric signal to the processing circuit 44.

The processing circuit 44 controls the overall workings of the X-ray CT apparatus 1. For example, the processing circuit 44 executes a control function 44*a*, a pre-processing function 44*b*, a first generation function 44*c*, a second generation function 44*d*, a third generation function 44*e*, a fourth generation function 44*f*, and an acquisition function 44*g*. Herein, for example, each of processing functions executed by the control function 44*a*, the pre-processing function 44*b*, the first generation function 44*c*, the second generation function 44*d*, the third generation function 44*e*, the fourth generation function 44*f*, and the acquisition function 44*g* being constituents of the processing circuit 44 illustrated in FIG. 1 is stored in the memory 41 in the form of a computer-executable computer program. The processing circuit 44 is, for example, a processor, and reads each computer program from the memory 41 and executes the computer program to realize the function corresponding to the read computer program. In other words, the processing circuit 44 that has read each computer program has the corresponding function illustrated in the processing circuit 44 in FIG. 1. The processing circuit 44 is an example reconstruction device.

The control function 44*a*, the pre-processing function 44*b*, the first generation function 44*c*, the second generation function 44*d*, the third generation function 44*e*, the fourth generation function 44*f*, and the acquisition function 44*g* are an example control section, pre-processing section, first generation section (generation unit), second generation section (correction unit), third generation section (selection unit), fourth generation section (reconstruction unit), and acquisition section, respectively. Furthermore, the control section is example display control unit.

Note that FIG. 1 illustrates a case where each of the processing functions of the control function 44*a*, the pre-processing function 44*b*, the first generation function 44*c*, the second generation function 44*d*, the third generation function 44*e*, the fourth generation function 44*f*, and the acquisition function 44*g* is implemented by a single processing circuit 44; however, the embodiment is not limited to this case. For example, the processing circuit 44 may be configured by combining a plurality of independent processors, and each processing function may be implemented by executing the corresponding computer program by the corresponding processor. Alternatively, each processing function of the processing circuit 44 may be implemented while appropriately being distributed among or integrated into a single or a plurality of processing circuits.

The control function 44*a* controls various types of processing on the basis of the input operations received from the operator via the input interface 43. Specifically, the control function 44*a* controls a CT scan performed by the gantry device 10. For example, the control function 44*a* controls workings of the X-ray high-voltage device 14, the X-ray detector 12, the control device 15, the DAS 18, and the table driving device 32 to control collection processing on the results of the counting at the gantry device 10. As an example, the control function 44*a* controls collection processing on projection data in a positioning scan for collecting a positioning image (scanogram image) and in scan (main scan) for collecting an image used for diagnosis.

Furthermore, the control function 44*a* causes the display 42 to display an image based on various pieces of image data or the like stored in the memory 41, as the display control unit.

The pre-processing function 44*b* generates projection data by performing pre-processing, such as logarithmic transformation processing, offset correction processing, sensitivity correction processing between channels, beam hardening correction, scattered radiation correction, and dark count correction, on the detection data output from the DAS 18.

The first generation function 44*c* generates CT image data by performing reconstruction processing using filtered back projection, iterative reconstruction, and the like on the projection data generated by the pre-processing function 44*b* and also generates sinogram data by performing forward projection processing on a CT image, as the generation unit. The first generation function 44*c*, the second generation function 44*d*, the third generation function 44*e*, and the fourth generation function 44*f* will be described in detail later.

The processing circuit 44 acquires various pieces of data from the X-ray detector 12, using the acquisition function 44*g*.

Next, the background according to the embodiment will be described in detail.

In cardiac computed tomography angiography (CTA), an artifact, such as a motion artifact, may appear in some cases. A possible method for removing such an artifact is to change the values of pixels in an image where it is considered that an artifact exists, using a deep learning or numerical analysis method or the like.

Unfortunately, with this method, image data itself is changed, so that anatomical information, such as a stricture, may be changed by artifact correction. Thus, it is desirable to correct an artifact without changing a value of image data.

The reconstruction device, the X-ray CT apparatus, and the image processing device according to the embodiment are based on this background, and the reconstruction device according to the embodiment includes the correction unit, the selection unit, and the reconstruction unit. The correction unit acquires a plurality of pieces of second sinogram data based on a plurality of pieces of first sinogram data. Specifically, the correction unit acquires the plurality of pieces of second sinogram data in which an artifact or noise is removed from the plurality of pieces of first sinogram data based on the plurality of pieces of first sinogram data. The selection unit acquires third sinogram data by comparing the first sinogram data with the second sinogram data and by selecting first sinogram data having close similarity. The reconstruction unit reconstructs an image on the basis of the third sinogram data.

The X-ray CT apparatus according to the embodiment includes the reconstruction device and the generation unit that generates the first sinogram data by performing X-ray CT scan. The image processing device according to the embodiment includes the reconstruction device and the display control unit that causes the display section to display the reconstructed image.

In this way, in the embodiment, the first sinogram data are merged on the basis of the second sinogram data subjected to artifact correction processing to generate the third sinogram data and, on the basis of this, a CT image is generated. In this method, the third sinogram data is based on information contained in any piece of the first sinogram data, so that the sinogram data values themselves are not changed. Thus, the X-ray CT apparatus 1 or the image processing device 40 according to the embodiment can perform motion correction while anatomical information of original data is retained, which improves image quality.

Figure 2:
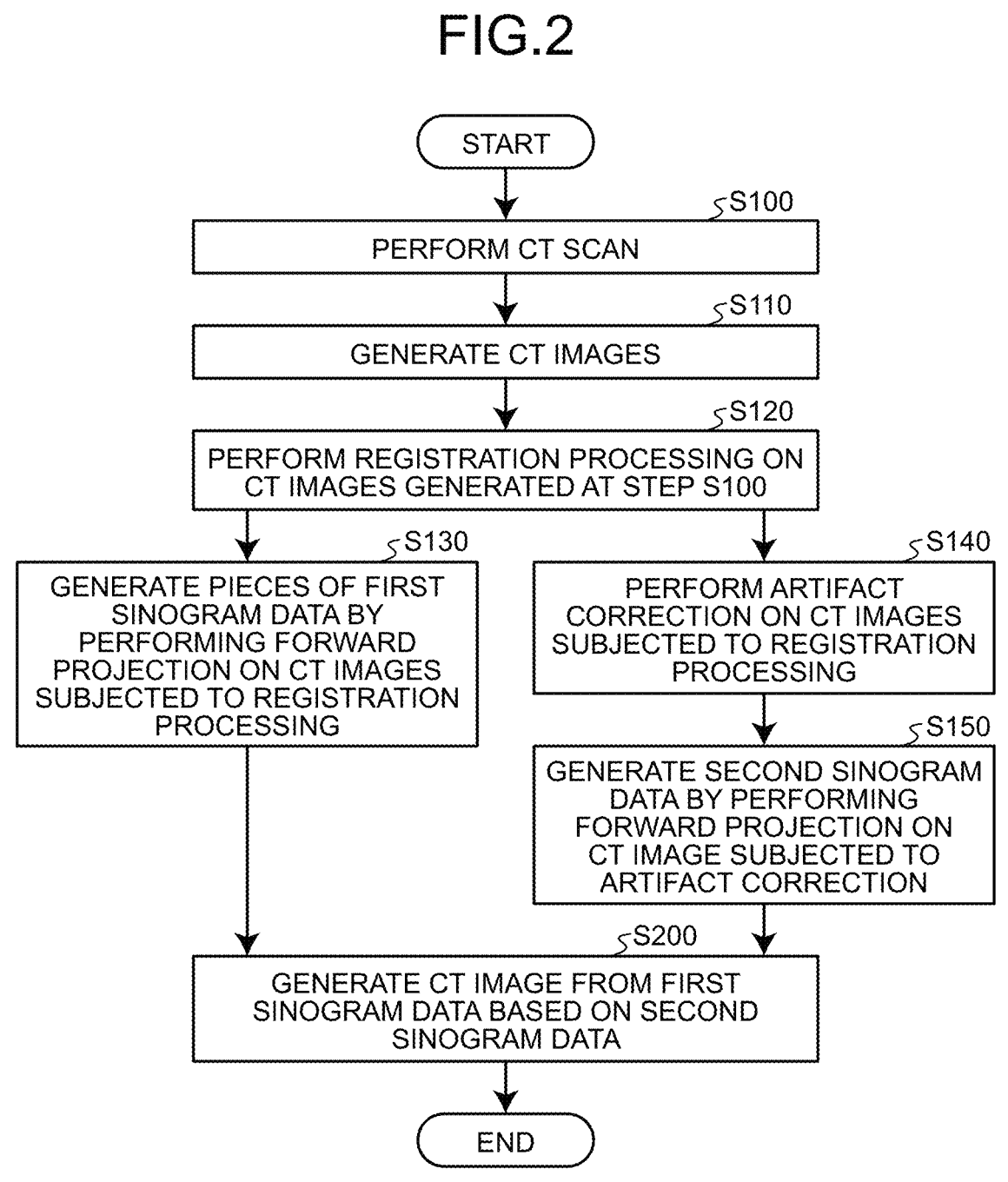
Figure 3:
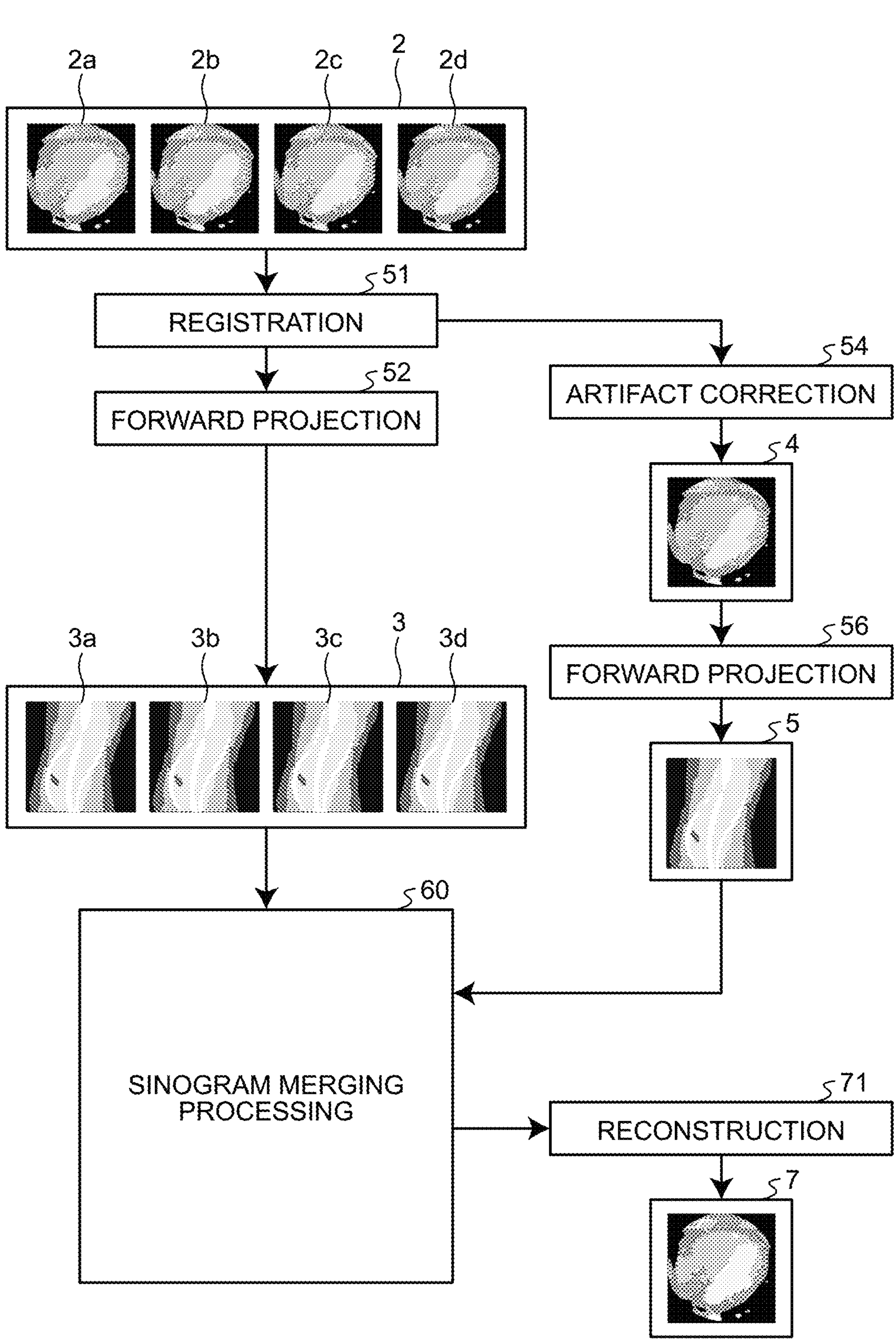
FIG. 3 is a diagram describing the processing performed by the X-ray CT apparatus according to the embodiment.

Next, processing performed by the X-ray CT apparatus 1 according to the embodiment will be described with reference to FIG. 2 and with appropriate reference to FIG. 3. FIG. 2 is a flowchart describing a flow of processing performed by the X-ray CT apparatus 1 according to the embodiment, and FIG. 3 is a schematic view describing the flow of the processing performed by the X-ray CT apparatus 1 according to the embodiment.

First, at Step S100, the X-ray CT apparatus 1 performs CT scan. Then, at Step S110, the processing circuit 44 generates a plurality of CT images 2 illustrated in FIG. 3 on the basis of the CT scan performed at Step S100, as the generation unit using the first generation function 44*c*. As an example, the processing circuit 44 generates a plurality of CT images 2*a*, 2*b*, 2*c*, and 2*d*, and the like by performing image reconstruction processing on data acquired on the basis of the CT scan performed at Step S100, as the generation unit using the first generation function 44*c*.

The CT images are, for example, time-series CT images being CT images acquired in the same scan in different time phases. In this case, at Step S100, the X-ray CT apparatus 1, for example, performs CT scan in a plurality of time phases in single scan. At Step S110, the processing circuit 44 generates the CT images 2*a*, 2*b*, 2*c*, and 2*d* on the basis of the CT scan performed at Step S100, as the generation unit using the first generation function 44*c*.

As another example, the CT images 2 generated at Step S110 may be CT images of mutually different heartbeats in the same time phase. That is, in this case, the CT images 2*a*, 2*b*, 2*c*, and 2*d* are CT images of different heartbeats in the same time phase.

As yet another example, the CT images 2 generated at Step S110 may be CT images acquired in mutually different scans. An example of the different scans, a scan for a coronary artery and a scan for myocardial scan can be an example case of cardiac scans. For example, a scan is performed at a tube voltage lowered in a scan for myocardial scan in comparison with a scan for a coronary artery, which are an example of the different scans. That is, in the example in FIG. 3, for example, the CT image 2*a* is a CT image relating to a scan for a coronary artery, and the CT image 2*b* to a scan for myocardial scan.

Note that, at Step S110, the processing circuit 44 may perform the image reconstruction processing and then pre-processing on the data acquired on the basis of the CT scan performed at Step S100 to generate the CT images 2. In this case, at Step S130, first sinogram data is generated on the basis of the CT images 2 generated by performing the pre-processing.

Then, at Step S120, the processing circuit 44 performs registration processing 51 on the CT images generated at Step S110, using the first generation function 44*c*. Specifically, the processing circuit 44 performs non-rigid registration as the registration processing 51 on the CT images generated at Step S110, using the first generation function 44*c*. For example, in a case of cardiac scan, this enables the processing circuit 44 to correct the effect of an influence of heart contraction or the like using the first generation function 44*c*.

At Step S130, the processing circuit 44 generates a plurality of pieces of first sinogram data 3, illustrated in FIG. 3, for the CT images 2 subjected to the registration processing 51 by performing forward projection on each of the images after the registration processing, as the generation unit using the first generation function 44*c*. Specifically, the processing circuit 44 generates each of the first sinogram data 3*a*, 3*b*, 3*c*, and 3*d* by performing forward projection 52 on the CT images 2*a*, 2*b*, 2*c*, and 2*d* after the registration processing, using the first generation function 44*c*. In this way, the processing circuit 44 generates the first sinogram data 3 by performing processing including the forward projection processing on each of the CT images, as the generation unit using the first generation function 44*c*.

Note that, at Step S130, the processing circuit 44 may perform the processing including the forward projection processing on each of the CT images and then predetermined pre-processing to generate the first sinogram data 3, as the generation unit using the first generation function 44*c*.

Returning to Step S120 in FIG. 2, at Step S140, the processing circuit 44 performs artifact correction processing 54 and the like on the CT images 2 subjected to the registration processing, as the correction unit using the second generation function 44*d*. Herein, the artifact correction processing 54 is, for example, processing correcting a motion artifact being an artifact caused by a motion of the subject. In this case, the processing circuit 44 generates an image 4 by performing the motion artifact correction processing on the CT images 2 subjected to the registration processing, using the second generation function 44*d*. The processing circuit 44 generates the image 4, for example, through processing using the adaptive motion correction (AMC) method of generating volume data in a target phase in which motion correction is applied and its preceding and subsequent phases from a range of exposed phases and estimating the amount of motion between volumes, processing by the image inference technique using the deep learning technique typified by a generative adversarial network (GAN), or the like, using the second generation function 44*d*. However, the embodiment is not limited to this, and the processing circuit 44 may generate the image 4 by another artifact correction method using the second generation function 44*d*.

As this artifact correction processing, the motion artifact correction is described; however, the embodiment is not limited to this, and the processing circuit 44 may perform processing for correcting a metal artifact or other artifacts as the artifact correction processing 54 at Step S140 to generate the image 4, using the second generation function 44*d*.

Then, at Step S150, the processing circuit 44 generates second sinogram data 5 by performing forward projection 56 on the image 4 being an image after subjected to the artifact correction processing 54, as the correction unit using the second generation function 44*d*. In this way, the processing circuit 44 generates the second sinogram data 5 by performing processing including the artifact correction processing 54 on the CT images 2, as the correction unit using the second generation function 44*d*. That is, the processing circuit 44 acquires a plurality of pieces of the second sinogram data 5 from the first sinogram data 3 by removing an artifact or noise at Steps S140 and S150, as the correction unit.

Figure 5:
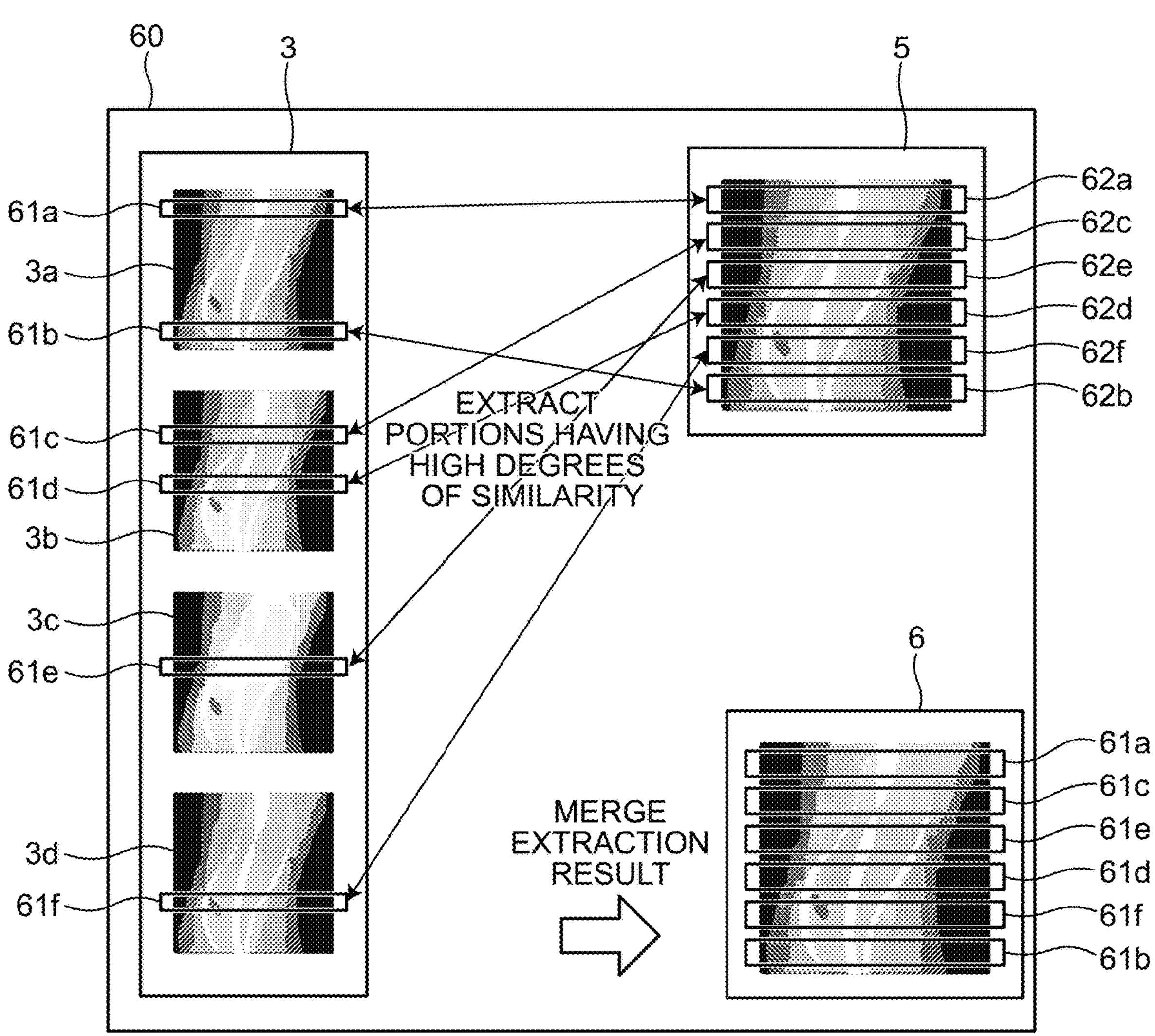
FIG. 5 is a diagram describing processing performed by the X-ray CT apparatus according to the embodiment.

Then, at Step S200, the processing circuit 44 performs sinogram merging processing 60 on the basis of the second sinogram data 5 to generate third sinogram data 6 illustrated in FIG. 5, which is described later, from the first sinogram data 3 and reconstructs the generated third sinogram data 6 through reconstruction processing 71 to generate a CT reconstructed image 7, as the selection unit using the third generation function 44*e*. That is, the processing circuit 44 compares the first sinogram data 3 with the second sinogram data 5 and selects first sinogram data having close similarity to acquire the third sinogram data 6 as the selection unit using the third generation function 44*e*, and reconstructs the image on the basis of the third sinogram data 6 as the reconstruction unit. The processing circuit 44 uses the second sinogram data 5 subjected to the artifact correction processing 54 as reference data for the merging processing 60, as the selection unit using the third generation function 44*e*.

Figure 4:
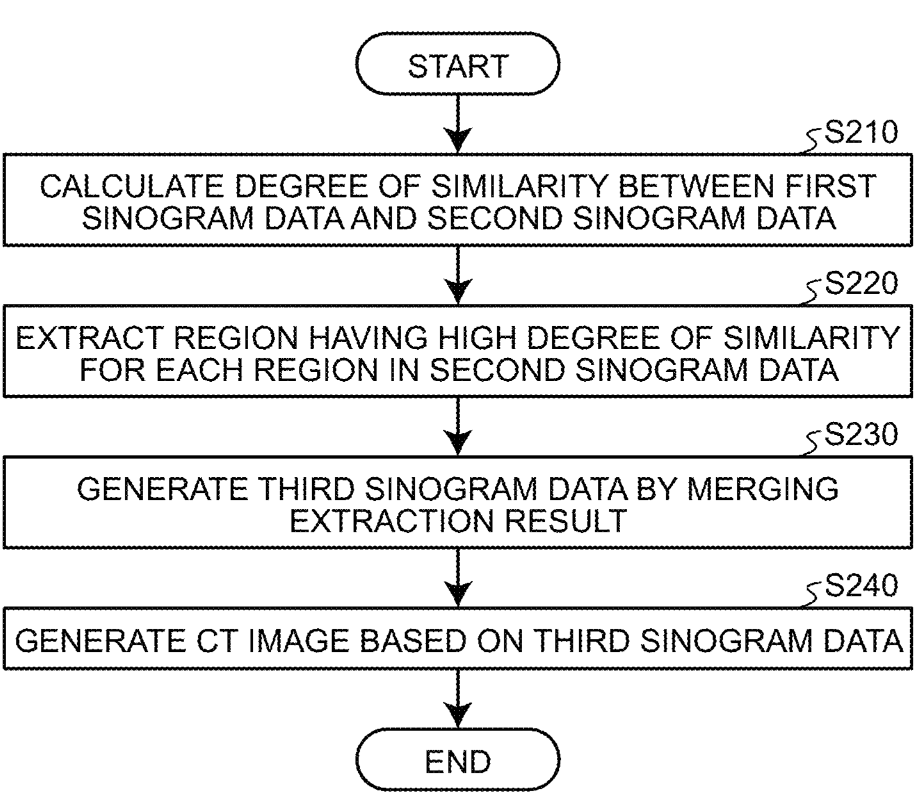
FIG. 4 is a flowchart describing processing at Step S200 in FIG. 2 in detail.

Step S200 will be described in detail below with reference to FIG. 4 and with appropriate reference to FIG. 5. FIG. 4 is a flowchart describing the processing at Step S200 in FIG. 2 in more detail. That is, the processing at Step S200 in FIG. 2 corresponds to processing at Steps S210 to S240 in FIG. 4. FIG. 5 is a diagram describing the sinogram merging processing 60 in more detail.

First, at Step S210, the processing circuit 44 calculates the degree of similarity between the first sinogram data 3 and the second sinogram data 5 as the selection unit using the third generation function 44*e*.

Then, at Step S220, the processing circuit 44 extracts a plurality of regions, in the first sinogram data 3, having a high degree of similarity to regions in the second sinogram data 5, for each region in the second sinogram data 5, as the selection unit using the third generation function 44*e*. For example, in FIG. 5, a region 61*a* in the first sinogram data 3*a*, a region 61*b* in the first sinogram data 3*a*, a region 61*c* in the first sinogram data 3*b*, a region 61*d* in the first sinogram data 3*b*, a region 61*e* in the first sinogram data 3*c*, and a region 61*f* in the first sinogram data 3*d* have high degrees of similarity to a region 62*a*, a region 62*b*, a region 62*c*, a region 62*d*, a region 62*e*, and a region 62*f* in the second sinogram data 5, respectively. Thus, the processing circuit 44 extracts the regions 61*a*, 61*c*, 61*e*, 61*d*, 61*f*, and 61*b* being regions, in the first sinogram data 3, having high degrees of similarity to the respective regions 62*a*, 62*c*, 62*e*, 62*d*, 62*f*, and 62*b* being regions in the second sinogram data 5, using the third generation function 44*e*.

Then, at Step S230, the processing circuit 44 generates the third sinogram data 6 by merging the result of the extraction at Step S220, as the selection unit using the third generation function 44*e*. Specifically, the processing circuit 44 generates the third sinogram data 6 illustrated in FIG. 5 by merging each of the first sinogram data 3 corresponding to the regions 61*a*, 61*c*, 61*e*, 61*d*, 61*f*, and 61*b* extracted at Step S220 into a single piece of sinogram data, using the third generation function 44*e*.

Then, at Step S240, the processing circuit 44 generates the CT reconstructed image 7 on the basis of the third sinogram data 6 as the reconstruction unit using the fourth generation function 44*f*.

As described above, at Step S200 composed of Steps S210 to S240, the processing circuit 44 calculates the degree of similarity between the first sinogram data 3 and the second sinogram data 5 and generates the third sinogram data 6 on the basis of the calculated degree of similarity, as the selection unit using the third generation function 44*e*, and generates the CT reconstructed image 7 on the basis of the generated third sinogram data 6.

Concerning the property of the generated third sinogram data 6, any region in the third sinogram data 6 generated at Step S200 has data of any portion in the first sinogram data 3 being the original data, and the data values themselves are not changed or processed.

In other words, it can be considered that the third sinogram data 6 are data subjected to the artifact correction while retaining the anatomical information of the first sinogram data 3. Thus, the X-ray CT apparatus 1 according to the embodiment can correct an artifact, such as a motion artifact, while anatomical information of original data is retained, which enables reduction in, for example, the possibility of making an erroneous diagnosis and the like.

According to at least one of the embodiments described above, image quality can be improved.

In the embodiments describe above, the example is explained in which the second generation function 44*d* as a correction unit performs the artifact correction processing 54 to the plurality of CT images 2. However, the embodiment is not limited to these cases. For example, as a generation function 44*d* as a correction unit, such processing to emphasize the position of the blood vessel or processing to move the image quality to be closer to that of user designation may be executed. By executing such processing, it becomes possible to obtain the image as the user desires.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A reconstruction device, comprising:
- a processing circuit configured to
  - acquire a plurality of pieces of second sinogram data based on a plurality of pieces of first sinogram data,
  - acquire third sinogram data by comparing the plurality of pieces of first sinogram data with the plurality of pieces of second sinogram data and by selecting pieces of first sinogram data, and
  - reconstruct and display an image based on the third sinogram data, wherein the processing circuit is further configured to
  - calculate a degree of similarity between the pieces of first sinogram data and the pieces of second sinogram data,
  - extract a region in the first sinogram data, for each of a plurality of regions in the pieces of second sinogram data:
  - generate the third sinogram data by merging a result of the extraction; and
  - generate the image based on the generated third sinogram data, and
- the processing circuit is further configured to generate the pieces of first sinogram data by performing registration processing on a plurality of CT images and then performing forward projection on each of the CT images after the registration processing, wherein the CT images are CT images of mutually different heartbeats in a same time phase, and the plurality of pieces of first sinogram data are sinogram data of mutually different heartbeats in a same time phase.

2. The reconstruction device according to claim 1, wherein the processing circuit is further configured to generate the second sinogram data by performing artifact correction processing on the CT images after the registration processing and performing forward projection on images after subjected to the artifact correction processing.

3. The reconstruction device according to claim 2, wherein the processing circuit is further configured to generate the pieces of first sinogram data by performing processing including pre-processing.

4. The reconstruction device according to claim 2, wherein the artifact correction processing is processing correcting a motion artifact.

5. The reconstruction device according to claim 1, wherein the CT images are time-series CT images being CT images acquired in same scan in different time phases.

6. The reconstruction device according to claim 1, wherein the CT images are CT images acquired in mutually different scans.

7. The reconstruction device according to claim 1, wherein
- the processing circuitry is further configured to acquire the plurality of pieces of second sinogram data in which an artifact or noise is removed from the plurality of pieces of first sinogram data based on the plurality of pieces of first sinogram data.

8. An X-ray CT apparatus, comprising:

a reconstruction device including a processing circuit configured to acquire a plurality of pieces of second sinogram data based on a plurality of pieces of first sinogram data, acquire third sinogram data by comparing the pieces of first sinogram data with the pieces of second sinogram data and by selecting pieces of first sinogram data, and reconstruct and display an image based on the third sinogram data, the X-ray CT apparatus being configured to generate the first sinogram data by performing an X-ray CT scan, wherein the processing circuit is further configured to calculate a degree of similarity between the pieces of first sinogram data and the pieces of second sinogram data, extract a region in the first sinogram data, for each of a plurality of regions in the pieces of second sinogram data:

generate the third sinogram data by merging a result of the extraction; and generate the image based on the generated third sinogram data, and the processing circuit is further configured to generate the pieces of first sinogram data by performing registration processing on a plurality of CT images and then performing forward projection on each of the CT images after the registration processing, wherein the CT images are CT images of mutually different heartbeats in a same time phase, and the plurality of pieces of first sinogram data are sinogram data of mutually different heartbeats in a same time phase.

9. An image processing device, comprising:

a reconstruction device including a processing circuit configured to acquire a plurality of pieces of second sinogram data based on a plurality of pieces of first sinogram data by removing an artifact or noise, acquire third sinogram data by comparing the pieces of first sinogram data with the pieces of second sinogram data and by selecting pieces of first sinogram, and reconstruct and display an image based on the third sinogram data, the image processing device being configured to cause a display to display the image, wherein the processing circuit is further configured to calculate a degree of similarity between the pieces of first sinogram data and the pieces of second sinogram data, extract a region in the first sinogram data, for each of a plurality of regions in the pieces of second sinogram data:

generate the third sinogram data by merging a result of the extraction; and generate the image based on the generated third sinogram data, and the processing circuit is further configured to generate the pieces of first sinogram data by performing registration processing on a plurality of CT images and then performing forward projection on each of the CT images after the registration processing, wherein the CT images are CT images of mutually different heartbeats in a same time phase, and the plurality of pieces of first sinogram data are sinogram data of mutually different heartbeats in a same time phase.

* * * * *